(12) United States Patent
Jelinek

(10) Patent No.: US 7,794,968 B2
(45) Date of Patent: *Sep. 14, 2010

(54) POLYDIACETYLENE-CONTAINING SOLID COLORIMETRIC AND/OR FLUORESCENT DETECTOR, METHOD FOR ITS PREPARATION AND USES THEREOF

(75) Inventor: Raz Jelinek, Reut (IL)

(73) Assignee: Ben-Gurion University of the Negev Research and Development Authority, Beer-Sheva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/328,472

(22) Filed: Jan. 9, 2006

(65) Prior Publication Data

US 2006/0172371 A1    Aug. 3, 2006

Related U.S. Application Data

(63) Continuation-in-part of application No. PCT/IL2004/000605, filed on Jul. 7, 2004.

(60) Provisional application No. 60/644,700, filed on Jan. 19, 2005.

(30) Foreign Application Priority Data

Jul. 10, 2003    (IL)    ................................ 156869

(51) Int. Cl.
    C12Q 1/04    (2006.01)
(52) U.S. Cl. ................. 435/34; 530/395; 536/123.1
(58) Field of Classification Search ............. 435/34; 536/123.1; 530/395
    See application file for complete search history.

(56) References Cited

U.S. PATENT DOCUMENTS 6,022,748 A * 2/2000 Charych et al. ............ 436/527

| 6,361,962 | B1 | 3/2002 | Lentini et al. ............ 435/29 |
| 6,548,268 | B1 * | 4/2003 | Rambach ............ 435/34 |
| 2002/0034475 | A1 | 3/2002 | Ribi ............ 424/9.6 |

FOREIGN PATENT DOCUMENTS

| WO | WO97/27316 | 7/1997 |
| WO | WO98/39632 | 9/1998 |
| WO | WO99/10743 | 3/1999 |
| WO | WO 00/55623 | 9/2000 |
| WO | WO2005/005623 | 1/2005 |

OTHER PUBLICATIONS

Pan, J. J. ET Charych, D,: "Molecular recognition and colorimetric detection of cholera toxin by poly(acetylene) liposomes incorporating Gml ganglioside"Langmuir, vol. 13, 1997, pp. 1365-1367.

Jelinek R. et al.: "Interfacial Catalysis by Phospholipases at Conjugated Lipid Vesicles: Colorimetric Detection and NMR Spectroscopy", Chemistry and Biology, Current Biology, London, GB, vol. 5, Nov. 1998, pp. 619-629.

Jelinek R. et al.: "Polymerized Lipid Vesicles as Colorimetric Biosensors for Biotechnology Applications", Biotechnology Advances, Elsevier Publishing, Barking, GB, vol. 19, No. 2, Apr. 1, 2001, pp. 109-118.

Rozner S et al.: "Detection and Analysis of Membrane Interactions by a Biomimetic Colorimetric Lipid/ Polydiacetylene Assay", Analytical Biochemistry, Academic Press, San Diego, CA, US, vol. 319, No. 1, Aug. 1, 2003, pp. 96-104.

International Search Report and Written Opinion from International Application No. PCT/IL2004/000605, completed Oct. 14, 2004 and mailed on Nov. 16, 2004.

* cited by examiner

*Primary Examiner*—Chih-Min Kam
(74) *Attorney, Agent, or Firm*—Heslin Rothenberg Farley & Mesiti P.C.

(57) ABSTRACT

The invention provides a colorimetric and/or fluorescent detector, which is a solid organic matrix, most preferably in the form of a gel, comprising polydiacetylene(s) and one or more lipids. Processes for preparing the detector and methods for using the same, including for the detection of microorganism suspected to be present in food products, are also provided.

20 Claims, 2 Drawing Sheets

US 7,794,968 B2

POLYDIACETYLENE-CONTAINING SOLID COLORIMETRIC AND/OR FLUORESCENT DETECTOR, METHOD FOR ITS PREPARATION AND USES THEREOF

CROSS REFERENCE TO RELATED APPLICATIONS

This application is a continuation-in-part of International Application No. PCT/IL2004/000605, filed Jul. 7, 2004 and published in English as WO 2005/005982 on Jan. 20, 2005, which claims the benefit of IL 156869 filed Jul. 10, 2003, and also claims priority of provisional application No. 60/644,700 filed Jan. 19, 2005, all of which applications are incorporated herein by reference in their entirety for all purposes.

FIELD OF THE INVENTION

The present invention relates to a solid calorimetric and/or fluorescent detector comprising polydiacetylene and lipids, exhibiting a visible color change or a characteristic fluorescence emission associated therewith, in response to the presence of an analyte. More specifically, the present invention provides a solid calorimetric and/or fluorescent detector that is particularly suitable for the rapid detection of microorganisms.

BACKGROUND OF THE INVENTION

Polydiacetylenes, a class of polymers obtained by the polymerization of diacetylene monomers (organic molecules containing two carbon-carbon triple bonds), exhibit two distinct absorption bands in the visible region. The art has suggested numerous detection methods for various chemical and biological analytes, based on the unique property of polydiacetylenes to undergo a visible color change from blue to red following a structural perturbation in their electronic conjugated backbone, which perturbation is generated by the analytes to be detected.

WO 98/39632 suggests the use of polydiacetylenes for detecting membrane conformational changes. In particular, membrane modifying reactions and analytes responsible therefore are discussed in said publication.

WO 99/10743 describes the encapsulation of polydiacetylenes into metal oxide glass, and the use of the transparent composite obtained for the detection of various analytes.

WO 00/55623 discloses a beneficial combination of polydiacetylenes, lipids and suitable means linked thereto for detecting the presence of analytes in a liquid sample, wherein said analytes cannot react chemically with said polydiacetylenes and lipids. Specifically mentioned analytes include metal ions, biological ligands and peptides.

U.S. Pat. No. 6,361,962 describes a multi-type toxin indicator which may comprise polydiacetylenes for detecting the presence of bacteria in foods.

U.S. 2002/0034475 discloses the incorporation of polydiacetylenes into various food products. The polydiacetylenes undergo a chromatic color transition in response to various triggering mechanisms such as temperature change, pH change, mechanical stress and the presence of bacteria in the food.

SUMMARY OF THE INVENTION

It is an object of the present invention to provide a highly sensitive, essentially solid polydiacetylene-containing detector, which responds rapidly to the presence of various analytes or by-products thereof.

It is another object of the present invention to provide an efficient process for producing such a detector.

It is yet another object of the present invention to provide methods for using the polydiacetylene-containing detector in determining the presence of various analytes on or within a substrate, and particularly, the presence of microorganism in various samples, including food products.

The inventor has found that a liquid mixture comprising diacetylene monomers (or the corresponding polymers), lipids and suitable liquid precursors of solid organic substances may be transformed, following solidification and optionally polymerization (in case that the diacetylene monomers were present in said mixture), into a novel chemical construct, typically in the form of a porous, gel-like solid organic matrix, which may be directly used for detecting the presence of various analytes. Thus, by appropriate selection of the organic substances from which the rigid, organic framework is made, the solid organic matrix comprising polydiacetylenes and lipids may allow the detection of various analytes, particularly microorganisms and by-products thereof.

The present invention is directed to a calorimetric and/or fluorescent detector, which is a solid organic matrix, preferably in the form of a gel-like solid, comprising one or more polydiacetylenes and one or more lipids.

By the term "calorimetric and/or fluorescent detector" is meant that the aforementioned solid organic matrix comprising polydiacetylene(s) and lipid(s) is capable of responding to the presence of various analytes by exhibiting a chromatic transition (e.g. a change in visible color of the matrix or a portion thereof) and/or a characteristic fluorescent emission associated therewith.

The term "solid organic matrix", as used herein, indicates a solid framework made of organic compounds and, more specifically, organic polymers, wherein the polydiacetylenes and lipids are incorporated within said solid framework. Preferably, the organic matrix is made of polymers that are capable of forming gel-like solid at room temperature, the melting point of said polymers being preferably above 25° C., and more preferably above 50° C. Particularly preferred polymers useful for forming the solid organic matrix according to the present invention are selected from the group consisting of polysaccharides and polyacrylamides. The term "polymers", as used herein, encompasses both homopolymers and copolymers.

A particularly preferred embodiment of the invention relates to a calorimetric and/or fluorescent detector, which is an organic matrix provided in the form of gel-like solid capable of supporting the growth of microorganisms, wherein the polydiacetylenes and the lipids are incorporated within said gel-like solid. Most preferably, the gel-like solid organic matrix is selected from the group consisting of agar, agarose and other natural or synthetic gelatinous polymers. According to this embodiment, nutrients required for the growth of microorganism are preferably present in the organic matrix.

The preparation of the solid organic matrix comprising polydiacetylenes and lipids according to the present invention involves the polymerization of the diacetylene monomers either before or after they become, together with the lipids associated therewith, assembled with the organic matrix. Unexpectedly, the solid organic matrix comprising polydiacetylenes and lipids, obtained by a process in which the polymerization step occurs after the incorporation of the diacetylene monomers and the lipids within the organic matrix, yields a product exhibiting excellent sensitivity towards various analytes that need to be detected. A particularly preferred embodiment of the invention relates to a calorimetric and/or fluorescent detector which is an organic matrix provided in the form of gel-like solid, wherein the polydiacetylenes and the lipids assembled therewith are homogeneously distributed within said gel-like solid.

Another aspect of the invention relates to a process for preparing a solid organic matrix comprising polydiacetylenes and lipids, which process comprises providing a suspension of one or more diacetylene monomers and one or more lipids, mixing said suspension with the liquid precursor of the organic substances of which the matrix is made, solidifying the resulting mixture and polymerizing the diacetylene monomer(s) present therein, to obtain a solid organic matrix containing chromatic polydiacetylenes and lipids.

Another aspect of the invention relates to a process for preparing a solid organic matrix comprising polydiacetylenes and lipids, which process comprises providing a suspension of diacetylene monomer(s) and said lipids, polymerizing the diacetylene monomer(s) present therein to obtain a suspension containing chromatic polydiacetylenes and lipids, mixing said suspension with the liquid precursor of the organic substances of which the matrix is made and solidifying the resulting mixture, to obtain a solid organic matrix comprising chromatic polydiacetylenes and lipids.

In another aspect, the present invention provides a method for detecting the presence of an analyte in a sample, comprising contacting the sample to be tested with a solid organic matrix comprising polydiacetylenes and lipids, and following a suitable incubation period, either observing the color of said matrix or the fluorescence emission thereof, wherein a change in said color (typically a blue to red transition) or a characteristic fluorescence emission (typically the emission at about 560 or 650 nm, following excitation at about 500 nm) indicate the presence of said analyte in the tested sample. Preferred analytes that may be detected by the method according to the present invention are species that are capable of interacting with cellular membrane. Most preferably, the analytes are selected from the group consisting of microorganisms and toxins produced thereby, metal cations, peptides, pharmaceutically active compounds, proteins and other biological ligands.

In a particularly preferred embodiment of the invention, there is provided a method for detecting the presence of microorganisms and/or toxins produced thereby in a sample, comprising contacting the sample to be tested with an organic matrix comprising polydiacetylenes and lipids, wherein the organic substances from which said matrix is formed are capable of supporting the growth of said microorganisms, and following a suitable incubation period, either observing the color of said matrix or the fluorescent emission thereof, wherein a change in said color or a characteristic fluorescent emission indicate the presence of said microorganism and/or toxins in the tested sample.

The above-described method may be used for the detection of any microorganism whose survival or growth may be supported by the organic matrix. However, according to a preferred embodiment of the invention, the microorganisms are bacteria.

It should be noted that the solid detector according to the present invention generates a localized, stable, easily visible color change in response to the presence of the tested analyte, unlike polydiacetylenes-based detectors that are provided in a liquid form, wherein the color transition induced by the presence of the analyte may become blurred or diluted.

It has been surprisingly found that the duration of the incubation period required in order to determine whether or not bacteria are present in the tested sample according to the method of the present invention may be much shorter than that required for the detection of bacteria by conventional techniques of microbial culture. Thus, in a preferred embodiment of the present invention, the above-described method for detecting the presence of microorganisms may be used for the rapid detection of bacteria in a sample, wherein the incubation period is less than the period of time required for the development of visible bacterial colonies.

In the Drawings:

All the above and other characteristics and advantages of the present invention will be further understood from the following illustrative and non-limitative description of preferred embodiments thereof.

DETAILED DESCRIPTION OF PREFERRED EMBODIMENTS

Figure 1:
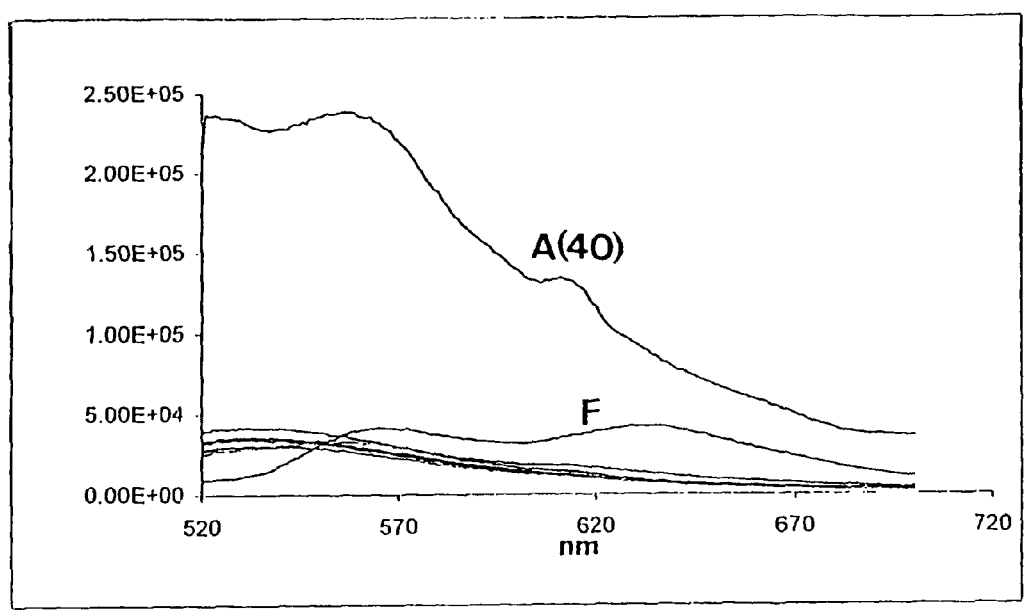
FIG. 1 shows the fluorescence spectrum of the organic matrix of the invention in the presence of E. coli.

Preferred diacetylene monomers that may be used according to the present invention for preparing the chromatic polydiacetylenes are well known in the art and are described, inter alia, in WO 99/10743 and US 2002/0034475, which are incorporated herein by reference.

Most preferably, the monomers are selected from the group consisting of 10,12-tricosadiynoic acid, 10,12-pentacosadiynoic acid, 10,12-octadecadiynoic acid, 5,7-docosadiynoic acid, 5,7-pentacosadiynoic acid and 5,7-tetracosadiynoic acid. These monomers are all commercially available.

Preferred lipids that may be used according to the present invention include, but are not limited to, glycolipids, phospholipids, lipopolysaccharides, steroids and alcohol derivatives thereof, extracts of lipids of the cell membrane obtained from various microorganisms as well as other components of the cell membrane. Particularly preferred lipids are selected from the group consisting of dimirystoylphosphatidylcholine (DMPC), phosphatidylglycerole (PG), dipalmitoylphosphatidylcholine (DPPC), natural phosphatidylcholine (PC), dimirystoylphosphatidylethanolamine (DMPE), cardiolipin, dimyristoylphosphatidylserine (DMPS), sphingomyelin, sphingolipids, ceramide, galactosylceramide, cholesterol, or mixtures thereof.

The preparation of an organic matrix comprising polydiacetylenes and lipids according to the present invention involves the dissolution of the diacetylene monomer and the lipids in one or more suitable organic solvents. Preferred solvents may be selected from the group consisting of alcohols, most preferred being lower alkanols such as methanol and ethanol, hydrocarbons, which may be optionally halogenated, such as chloroform, and aromatic hydrocarbons, such as benzene and toluene. Preferably, the molar ratio between the diacetylene monomer and the lipid that are mixed in the solvent system described above is in the range of 2:3 to 10:1, wherein a molar ratio of about 1:1 is most preferred.

Following the removal of the organic solvent(s), preferably by drying the organic solution in vacuo, water is added to the solid mixture of diacetylene monomer and lipid to form an aqueous suspension. The volume of water should be such that the concentration of the resulting suspension, calculated according to the total amount of the monomer and lipid, is between 1 mM to 7 mM, more preferably between 4 mM to 6 mM, most preferably about 5 mM.

The aqueous suspension is subjected to probe-sonication at elevated temperature, preferably in the range of 60 to 80° C.

The duration of the sonication is dependent on the power generated by the sonicator. For example, for a sonicator of 100 W power, with short intermission between the sonication pulses, the duration of the sonication is between 3 to 5 minutes. Alternatively, the aqueous suspension may be subjected to bath sonication or to extraction through extrusion.

According to a particularly preferred variant of the present invention, the hot mixture of diacetylene monomers and lipids obtained upon completion of the sonication stage, is mixed under elevated temperature at the range between 60 to 90° C. with the organic substances that are intended for constructing the final porous organic matrix of the present invention, wherein said organic substances are provided at this stage of the synthetic procedure in a liquid form, typically as a liquid suspension (also designated in the present text as "the liquid precursor of the organic substances of which the matrix is made"), such that they may become intimately mixed with the diacetylene monomer and the lipids. According to a particualrly preferred embodiment of the invention, the liquid precursor of the organic substances of which the matrix is made is provided in the form of a liquid suspension (pre-gelatenous) of agar or agraose. It should be noted that if the final product is intended for the detection of microorganisms or by products thereof, suitable nutrients (such as yeast extract and broth), needed for the growth of said microorganisms, are also included in said liquid precursor.

Compositionally, the ratio between the volume of the aqueous suspension containing the diacetylene and the lipids (in typical concentration of about 1 to 7 mM), to the volume of the liquid precursor of the organic substances of which the matrix is made, is in the range of 1:3 to 1:20, and more preferably between 1:5 to 1:11, most preferred being a ratio of about 1:8.

Having mixed the aqueous suspension of the diacetylene and the lipids with the liquid precursor of the organic substances of which the matrix is made, the resulting suspension is allowed to gradually cool down and is maintained at 4° C. for at least 6 hours, following which the solidified organic matrix that contains the diacetylene monomer and the lipids is irradiated at 254 nm for about 10 to 50 seconds, preferably by means of UV oven (cross linker) or UV lamp, to polymerize the diacetylene monomer, thus producing the final, blue organic matrix containing polydiacetylenes and lipids.

Alternatively, the solid organic matrix comprising polydiacetylenes and lipids may be prepared by a process comprising the following steps: providing a suspension of a diacetylene monomer and said lipids, polymerizing the diacetylene monomer present therein to obtain a suspension containing chromatic polydiacetylenes and lipids, mixing said suspension with the liquid precursor of the organic substances of which the matrix is made at a temperature of about 26 to 31° C., and preferably at a temperature of about 27 to 30° C., and solidifying the resulting mixture, to obtain a solid organic matrix comprising chromatic polydiacetylenes and lipids. The preparation of the suspension of the diacetylene monomer and the lipids and the subsequent polymerization step are carried out under the conditions described above.

The resulting solid organic matrix comprising the polydiacetylene and the lipid exhibits blue color and may be easily and conveniently applied for rapidly detecting the presence of various analytes that are capable of interacting with cellular membrane, such as microorganisms and toxins produced thereby, metal cations, peptides, proteins, biological ligands and pharmaceutically active compounds. In general, it is sufficient to place the sample to be tested on the surface of the solid organic matrix, and following a suitable incubation period, which depends on the type of the analyte, observing the color of said matrix, wherein a change in said color indicates the presence of said analyte in the tested sample. A minimal concentration of the analyte, that is detectable by the method of the invention, is typically in the range between 1 $\mu$M to 1 mM. Typical incubation periods may vary between 0.1 to 30 minutes for ligands selected from the group consisting of metal cations, peptides, pharmaceutically active compounds, proteins and other biological ligands.

Metal cations that may be detected according to the present invention include alkali or alkaline-earth metals, as well as transition metals.

Peptides that may be detected by the method of the present invention include antimicrobial peptides, membrane-active peptides and cytolytic peptides. The peptides may contain between 5 to 100 amino acids, and may have hydrophobic and amphipathic domains.

Pharmaceutically active compounds that may be detected by the method of the present invention include, but are not limited to, hydrophobic compounds having molecular weight of below 1000 g/mol, that are capable of binding and permeating cellular membrane or physiological lipid barriers, such as drugs, metabolites and penetration enhancers.

Proteins that may be detected by the method of the present invention include, but are not limited to, membrane proteins, lipophilic enzymes and signaling proteins. Other biological ligands that may be detected by the method of the present invention include hormones and biological compounds that specifically bind or permeate cellular membranes or have specific affinities to membrane receptors.

One preferred embodiment of the invention relates to the detection of microorganisms and/or toxins produced thereby. The microorganisms that may be detected by the method according to the present invention include, inter alia, bacteria and fungi. Typical incubation time may vary between 3 to 13 hours.

In a particularly preferred embodiment of the present invention, the method disclosed and described herein is used to detect the presence of microorganisms and/or their toxins in food products. In one mode of operation, samples of either the solid food product (e.g. meat, hard cheese, etc.) or liquid food product (e.g. milk or juice) are streaked onto the surface of an organic matrix (e.g. nutrient agar) comprising polydiacetylene and lipid, said organic matrix being contained within a Petri dish. In the event that the food sample contains microorganism or their toxins, a color change of the matrix is observed within 3 to 13 hours following incubation of the Petri dish at a temperature of between 24° and 30° C. It is to be emphasized that, in the case of bacterial contamination, this color change may be observable even when no bacterial colonies are visible on the agar surface.

In an alternative embodiment, the organic matrix comprising polydiacetylene and lipid may be incorporated into the packaging of a food product. In this way, possible deterioration of a food product due to, for example, microbial contamination, may be detected as a distinct blue-to-red color change of the packaging. In order to enhance readability, the above-mentioned organic matrix may be spatially arranged within the food packaging such that upon changing color, a distinct symbol or word becomes visible. Thus, if the organic matrix of the present invention were to be incorporated in the form of the letter 'X' in a portion of the packaging having exactly the same color as the polydiacetylene and lipid-containing organic matrix, microbial contamination of the food product would be indicated by the presence of a red letter 'X' set in a blue background.

The particularly preferred calorimetric and/or fluorescent detector provided by the present invention, which is an organic matrix provided in the form of a gel-like solid capable of supporting the growth of microorganisms, which gel-like solid comprises one or more polydiacetylenes and one or more lipids, (e.g., nutrient agar containing one or more polydiacetylenes and one or more lipids) may be also used for detecting the presence of bacteria in samples of body fluids, such as urine, blood and spinal cord fluid. Thus, the urine sample or the blood sample to be tested is placed on the surface of the organic matrix, and following a suitable incubation period at about 27° C., a visible blue to red color change of said matrix, or the detection of a characteristic fluorescence emission, indicate the presence of bacteria in the tested sample.

In another embodiment, water samples (e.g., of clean water, treated water and sewage) may be contacted with the organic matrix provided in the form of a gel-like solid capable of supporting the growth of microorganisms, which gel-like solid comprises one or more polydiacetylenes and one or more lipids, in order to determine the presence of microorganism in the tested water sample.

The blue to red transition exhibited by the organic matrix comprising polydiacetylene and lipids according to the detection methods described herein can be observed by the naked eye. Alternatively, the color changes may be recorded by means of UV-vis spectrophotometer or an ELISA plate reader. Typically, the spectrophotometric reading is made at 27° C. using a 1 cm optical path cell with a standard laboratory spectrophotometric device such as the Jasco spectrophotometer. The quantitative measurement of the color transition exhibited by the organic matrix comprising polydiacetylene and lipids in the presence of the analyte may be carried out similarly to the description given in WO 00/55623, which is incorporated herein by reference.

Alternatively, the detection methods provided by the present invention, which have been described above in respect to various analytes, may be based on the characteristic fluorescent emission associated with the changes in the organic matrix comprising polydiacetylene and lipids that occur in response to the presence of the analyte. Detection of this fluorescent emission may be accomplished by illuminating the surface of the solid organic matrix with a suitable light source emitting light at about 495-505 nm. The appearance of characteristic maxima at about 560 and/or 650 nm in the fluorescence spectrum obtained following said excitation serves as an indication for the presence of the tested analyte. The aforementioned procedure may be suitably carried out using an inverted microscope fitted with fluorescent excitation and detection means, or a standard fluorescence spectrophotometer.

It should be noted that when the organic matrix is intended for the detection of bacteria, and is thus made of a gel-like solid comprising one or more polydiacetylenes and one or more lipids, wherein the gel-like solid is capable of supporting the growth of microorganisms (e.g., nutrient agar containing one or more polydiacetylenes and one or more lipids), then the detection method that is based on the characteristic fluorescent emission associated with the changes in said organic matrix that occur in response to the presence of bacteria, as described hereinabove, is especially advantageous. Despite the fact that in many cases bacterial colonies may be observed on the surface of the organic matrix only after a relatively long incubation period (for example, actual visible colonies of *E. coli* JM101 and *Salmonella typhimurium* appear following an incubation period of approximately ten hours), it is possible to determine the presence of bacteria in the tested sample by contacting the same with the organic matrix and following an incubation period that is less than the period of time required for the development of visible bacterial colonies, producing fluorescent images of said organic matrices (for example, using an ELISA fluorescence reader, wherein the excitation is at 495 nm and the emission is at 560 nm), thereby readily confirming the presence of the bacteria in the tested sample. For the specific bacterial species mentioned above, an incubation period of about three hours was found sufficient.

It has been observed that the preferred calorimetric detector provided by the present invention, which is an organic matrix made of a gel-like solid comprising one or more polydiacetylenes and one or more lipids, wherein the gel-like solid is capable of supporting the growth of microorganisms (e.g., nutrient agar containing one or more polydiacetylenes and one or more lipids), may be also used for distinguishing between bacterial species.

More specifically, it has been observed that the development of a bacterial colony on the surface of the calorimetric detector of the present invention induces the formation of a red halo around the colony. By the term "red halo" is meant an essentially annular region which extends radially from the boundaries of the colony, circumferentially surrounding the same, wherein the color of said region has been transformed from blue (the original color of the detector) to red due to the presence of the bacteria. It has been found that the value of the ratio between the radius of a bacterial colony (designated $r_{colony}$), and the radius of the red halo surrounding the same (designated $r_{halo}$ and given by the difference between $r_{total}$ and $r_{colony}$, wherein $r_{total}$ is the radius of the total area occupied by the colony and the halo) depends on the identity of the bacterial species and the composition of the organic matrix. For example, in an organic matrix which comprises agar, DMPG, and PDA, the ratio $r_{halo}:r_{colony}$ for *E. coli* was 1.0, while in an organic matrix which comprises agar, DMPC, and PDA, this ratio was 1.2. The corresponding values for *Salmonella typhimurium* (wild type) were 2 and 4, respectively. It is therefore possible to obtain, for each bacterial species, a set of reference values comprising ratios $r_{halo}:r_{colony}$ produced in a plurality of colorimetric detectors having different compositions (e.g., organic matrices containing different lipids). The resulting set of reference values generated for a given bacterial species, which may be represented as follows:

$$\{r_{halo}:r_{colony}(1), r_{halo}:r_{colony}(2), \ldots r_{halo}:r_{colony}(k)\}_{bacteria\ x}$$

wherein the integer in parentheses identifies an organic matrix of specific composition in which the ratio $r_{halo}:r_{colony}$ was calculated for bacteria of the given species (bacteria x), may thus serve as a "fingerprint" or "identification number" of said bacteria.

Accordingly, the present invention further provides a method for determining the presence of specific bacterial strains in a sample, which comprises:

providing a plurality of organic matrices, each of which containing polydiacetylenes, lipids and organic substances that are capable of supporting the growth of bacteria, wherein said organic matrices are compositionally distinct from one another;

contacting one or more samples to be tested with each of said plurality of organic matrices;

determining, following a suitable incubation period and the development of one or more colonies in each of said matrices, the ratio $r_{halo}:r_{colony}$ for each colony developed in each of said matrices, to generate a group of numerical values associated with each matrix;

comparing the resultant groups of numerical values with one or more sets of reference values (obtained as described hereinabove), each set having the form:

$$\{r_{halo}:r_{colony}(1), r_{halo}:r_{colony}(2), \ldots r_{halo}:r_{colony}(k)\}_{bacteria\ x}$$

and determining the presence or absence of said specific bacterial strains (bacteria x) in said sample.

In another aspect, the present invention relates to an organic matrix made of a gel-like solid capable of supporting the growth of microorganisms, which comprises, in addition to one or more polydiacetylenes and one or more lipids, also one or more antibiotic compounds, (e.g., nutrient agar containing one or more polydiacetylenes, one or more lipids and at least one compound exhibiting antibacterial activity). The inclusion of an antibiotic compound within the organic matrix of the present invention is suitably carried out by dissolving or suspending said antibiotic compound in the liquid mixture containing the gel precursor, the lipids and the polydiacetylene (or the monomer precursors thereof) at any stage prior to the final solidification step yielding the gel-like organic matrix. The concentration of the antibiotic compound in the aforementioned liquid mixture is generally between 1 to 50 μg/ml.

Bacterial strains that are resistant to the specific antibiotic compound incorporated in the organic matrix (or mutants in which resistance was added through genetic engineering), will be able to grow in the organic matrix of the present invention, and induce the chromatic change, or the characteristic fluorescence emission described above.

For example, the growth of *salmonella typhimurium* wild type, kanamycin-resistant *salmonella typhimurium* and *E. Coli* MC4100 strain in an agar matrix containing polydiacetylene and lipids induces a visible color change from blue to red, or the characteristic fluorescence emission. However, when the agar matrix further comprises the antibiotic compound kanamycin, the blue to red color transition, or the characteristic fluorescence emission, will be observed for an agar matrix that has been contacted with kanamycin-resistant *salmonella*, but not for an agar matrix that has been contacted with the other two bacterial species mentioned above. On the other, the inclusion of streptomycin in agar matrices containing polydiacetylene and lipids will prevent the blue to red color change (or the corresponding characteristic fluorescence emission) in the case of *salmonella typhimurium* wild type and kanamycin-resistant *salmonella typhimurium*, but not in the case of *E. Coli* MC4100 which is resistant to streptomycin.

Thus, in another aspect, the present invention provides a method for determining the antibiotic resistance of bacterial strain, which comprises contacting the bacterial strain to be tested with an organic matrix comprising polydiacetylenes, lipids and an antibiotic agent, wherein the organic substances from which said matrix is formed are capable of supporting the growth of said microorganisms, and following a suitable incubation period, either observing the color of said matrix or detecting a fluorescent emission thereof, wherein a change in said color or a characteristic fluorescence emission indicate that said bacterial strain is resistant to said antibiotic agent.

As described in detail hereinabove, the particularly preferred organic matrix provided by the present invention, which is made of a gel-like solid capable of supporting the growth of microorganisms, wherein said gel-like solid comprises one or more polydiacetylenes and one or more lipids, is most preferably obtained by mixing a solution containing the diacetylene monomers and lipids with a sterilized suspension of a gel-forming material and nutrients. The resulting mixture is allowed to solidify and the diacetylene monomers are subsequently polymerized to form the blue organic matrix suitable for use as a calorimetric and/or fluorescent detector. It should be noted that the solid composition which contains the diacetylene monomers, the lipids, the gel-forming material (e.g., agar) and the nutrients may be conveniently used as a precursor for the final, blue polymerized matrix. This precursor may be stored, and prior to use may be suitably sterilized and molded into desired shapes and configurations according to the intended use. Following solidification of the mixture in the mold and polymerization of the diacetylene monomers (by means of radiation) under the conditions described hereinabove, the final blue, suitably shaped organic matrix is obtained. This radiation-polymerizable mixture which comprises diacetylene monomers, lipids and a gel-forming material capable of supporting the growth of microorganisms forms another aspect of the present invention.

The present invention includes within its scope many other applications of the basic polydiacetylene and lipid-containing organic matrix, and is not to be considered as being limited to only those embodiments described in detail in the following examples.

EXAMPLES

Example 1

Preparation of Organic Matrix Containing Polydiacetylenes and Lipid

Monomer: 10,12-tricosadiynoic acid
Lipid: dimirystoylphosphatydilcholine (DMPC)
Organic matrix: agar 20.8 mg of 10,12-tricosadiynoic acid (GFS chemicals, Powell, Ohio) were dissolved in a vessel containing 1 ml of chloroform and ethanol (1:1 v/v), to form a first stock solution. 27.1 mg of DMPC (Sigma-Aldrich) were dissolved in a separate vessel containing 1 ml of chloroform and ethanol (1:1 v/v), to form a second stock solution. Aliquots (20 μl) were taken from each of the two stock solutions and were mixed to form a series of 40 μl samples. Each of the samples prepared, containing 410 μg of the monomer and 540 μg of the lipid, was treated according to the following procedure.

The sample was dried in vacuo, to remove the organic solvents, and following the addition of 2 ml of deionized water, the resulting aqueous suspension was subjected to sonication at a temperature of 70° C. for 2 to 3 minutes by means of a probe-sonicator. Following sonication, the hot suspension was mixed with 8 ml taken from a nutrient agar solution prepared by dissolving 12 g of agar-agar (Conda SA), 10 g of NaCl, 10 g of peptone (Conda SA) and 5 g of yeast extract (Conda SA) in 1000 ml water, following which said solution was sterilized in an autoclave. 5 ml of the resulting mixture containing the monomer, the lipid, the agar and the nutrients were added to a 50 mm diameter Petri dish and allowed to solidify at room temperature. The organic matrix containing the 10,12-tricosadiynoic acid monomer and the lipid was kept at 4° C. overnight, following which it is irradiated at 254 nm for 10 to 20 seconds using UV cross linker (Stratagen) to yield a solid, blue agar matrix comprising the polydiacetylene and the lipid.

Example 2

Preparation of Organic Matrix Containing Polydiacetylenes and Lipid

Monomer: 10,12-tricosadiynoic acid
Lipid: dimirystoylphosphatydilcholine (DMPC)
Organic matrix: agar 20.8 mg of 10,12-tricosadiynoic acid (GFS chemicals, Powell, Ohio) were dissolved in a vessel containing 1 ml of chloroform and ethanol (1:1 v/v), to form a first stock solution. 27.1 mg of DMPC (Sigma-Aldrich) were dissolved in a separate vessel containing 1 ml of chloroform and ethanol (1:1 v/v), to form a second stock solution. Aliquots (20 µl) were taken from each of the two stock solutions and were mixed to form a series of 40 µl samples. Each of the samples prepared, containing 410 µg of the monomer and 540 µg of the lipid, was treated according to the following procedure.

The solution was dried in vacuo, to remove the organic solvent, and following the addition of 2 ml of deionized water, the resulting aqueous suspension was subjected to sonication at a temperature of 70° C. for 2 to 3 minutes by means of probe sonicator. Following sonication, the hot suspension was cooled and kept at 4° C. overnight, irradiated at 254 nm for 10 to 20 seconds using UV cross linker (Stratagen), to form a blue vesicle solution, which was mixed with 8 ml of a nutrient agar solution (prepared by dissolving 12 g of agar-agar (Conda SA), 10 g of NaCl, 10 g of peptone (Conda SA) and 5 g of yeast extract (Conda SA) in 1000 ml water, following which said nutrient agar solution was sterilized in an autoclave and was allowed to cool down to about 30° C., at which temperature the blue vesicle solution was mixed therewith) to obtain a homogeneous blue suspension. The resulting suspension was rapidly added to a 50 mm diameter Petri dish and allowed to solidify at room temperature, yielding the final solid, blue agar matrix comprising the polydiacetylene and the lipid.

Examples 3-7

Detecting the Presence of Microorganisms

A 50 mm-diameter Petri dishes containing solid organic matrices prepared according to Example 1 or 2 were used to detect the presence of microorganisms. To this end, various microbial colonies were seeded on the surface of the solid organic matrix, either by using an inoculating loop or by placing drops of said colonies on said surface. In addition, food products subjected to analysis were brought into contact with the inoculating device, such that it was possible to spread samples thereof on the surface of the solid organic matrix. The Petri dishes were then placed in an incubator set to a temperature of between about 24° C. and 30° C. The appearance of red spots indicated the presence of microorganisms. The following table summarizes the results obtained by the assays described above.

TABLE 1

| Example no. | microorganism/food product | Chromatic transition (Blue to red) |
|---|---|---|
| 3 | E. coil | Observed (incubation period - 9 h) |
| 4 | Bacillus | Observed (incubation period - 9 h) |
| 5 | Milk that was left out doors for 1 day | Observed (incubation period - 9 h) |
| 6 | Liver that was left out doors for 1 day | Observed (incubation period - 9 h) |
| 7 | Cooked liver that was left out doors for 1 day | Not observed |

Example 8 (Comparative)

The preparative procedure of Example 1 was repeated, without including any lipids in said procedure, such that the resulting solid organic matrix contained polydiacetylene, but not lipids. 50 mm-diameter Petri dishes containing the solid organic matrix obtained were used according to the assay procedures of the preceding examples. A blue to red color transition was not observed in any of these dishes.

Example 9

Preparation of Organic Matrix Containing Polydiacetylene and Lipid

Monomer: 10,12-tricosadiynoic acid
Lipid: dimirystoylphosphatydilcholine (DMPC)
Organic matrix: agarose The preparative procedure according to example 1 was repeated, with the stock solution of the agar and nutrients being replaced with an aqueous stock solution of agarose in water (2.5% w/v), to form a solid, blue agarose matrix comprising the polydiacetylene and the lipid in a Petri dish. The agarose used for preparing the matrix was obtained from Conda SA. This procedure was also repeated with the solidification of the blue organic matrix occurring in the cells of an Elisa plate (Jena Analytic).

Examples 10 to 17

Detecting the Presence of Various Analytes

Agarose matrices prepared according to Example 9, placed either in a 50 mm diameter Petri dish or in the 96-well plate (Jena Analytic), were used for detecting various analytes. The following stock solutions were prepared (the materials were obtained from Sigma-Aldrich):

An aqueous stock solution containing the peptide melittin at a concentration of 1 mg/ml.
An aqueous stock solution containing the peptide polymyxin-B at a concentration of 1 mg/ml.
An ethanolic stock solution containing oleic acid at a concentration of 1 mg/ml.
An ethanolic stock solution containing lidocaine at a concentration of 1 mg/ml.
An ethanolic stock solution containing diclofenac at a concentration of 1 mg/ml.
An aqueous stock solution containing $Zn^{2+}$ ions at a concentration of 50 mM (salt used: zinc sulfate).
An aqueous stock solution containing $Mg^{2+}$ ions at a concentration of 50 mM (salt used: magnesium sulfate).
An aqueous stock solution containing $Ca^{2+}$ ions at a concentration of 50 mM (salt used: calcium chloride).

A sample of about 5 to 10 µL was taken from each of the stock solutions described above, and was placed on the surface of the agarose matrix (either on the Petri dish, or within the cells of the 96-well plate). The Petri dishes and the plate were placed in an incubator at 27° C. The results obtained are summarized in the following table.

TABLE 2

| Example no. | Analyte | Chromatic transition (Blue to red) |
|---|---|---|
| 10 | Melittin (peptide) | Observed (incubation period - 10 minutes) |
| 11 | Polymyxin-B (peptide) | Observed (incubation period - 5 minutes) |
| 12 | Oleic acid | Observed (incubation period - 5 minutes) |
| 13 | lidocaine | Observed (incubation period - 5 minutes) |
| 14 | diclofenac | Observed (incubation period - 5 minute) |
| 15 | Zinc cation ($Zn^{2+}$) | Observed (incubation period - 1 minute) |
| 16 | Magnesium cation ($Mg^{2+}$) | Observed (incubation period - 1 minute) |
| 17 | Calcium cation ($Ca^{2+}$) | Observed (incubation period - 1 minute) |

Example 18

The Use of the Novel Construct as a Fluorescent Detector

This example illustrates that the organic matrix comprising polydiacetylene and lipids may be effectively used for detecting the presence of bacteria on the basis of a fluorescence emission.
1) A culture of *Escherichia coli* was prepared in 20 ml of LB medium, and incubated overnight at 37° C.
2) The preparation of glass slides having on their surface the solid organic matrix of the invention, and various comparative matrices:
(i) An aqueous suspension containing 10, 12-tricosadiynoic acid and DMPC was prepared according to the description given in Example 1, followed by sonication for 13 minutes (including a heating period of 3.5 minutes). The hot suspension obtained was then mixed with a hot nutrient agar solution (which was prepared in accordance with the description of Example 1) in a volume ratio of 1:2, to form a hot mixture containing the monomer, the lipid, the agar and the nutrients. One drop of this mixture was placed on each of several glass slides (which were previously cleaned with acetone). Each of these glass slides was subsequently covered with a second, silane-treated slide, in order to flatten the drop into a thin film on the surface of the first slide. The upper slides were removed after several minutes, and the glass slides carrying the composition comprising the monomer, the lipid, the agar and the nutrients were kept at 4° C. overnight, following which it is was irradiated at 254 nm for 24 seconds using UV cross linker (Stratagen) to yield a solid, blue agar matrix comprising the polydiacetylene and the lipid in the form of a thin film over the surface of the slide.
In addition, the following glass slides were prepared in a similar manner:
(ii) A glass slide having a thin film of the nutrient agar, containing neither the polydiacetylene nor lipids.
(iii) A glass slide having a thin film of the agar matrix comprising the diacetylene monomer and the lipid (that is, the final polymerization step according to the preparative procedure of (i) has been omitted).
(iv) A glass slide having a blue agar matrix comprising the polydiacetylene and the lipid in the form of a thin film over the surface of the slide, prepared according to the procedure (i) above, was subsequently heated for several seconds to induce the blue to red color transition.
3) The aforementioned glass slides were treated under various conditions, to define a suitable control group (in which none of the slides was brought into contact with the bacteria). The following table describes six glass slides, identified by the letters A-F, wherein said glass slides have been obtained from the aforementioned glass slides numbered (i)-(iv) in a manner described in the table.

TABLE 3

| Glass Slide | Preparation |
|---|---|
| A | Glass slide (i) without any further treatment |
| B | Glass slide (i) + a drop of LB medium |
| C | Glass slide (ii) without any further treatment |
| D | Glass slide (iii) without any further treatment |
| E | Glass slide (iii) + a drop of LB medium |
| F | Glass slide (iv) + a drop of LB medium |

4) A drop of the *e. coli* culture was added to the glass slide designated A (that is, the glass slide having on its surface the blue agar matrix comprising the polydiacetylene and the lipid), and fluorescence spectra were measured for this glass slide immediately after said addition and 10, 20 and 40 minutes following said addition. Fluorescence spectra were also obtained for several control glass slides. All these measurements were made using FL-920 Edinburgh spectrofluorimeter, and the results are shown in FIG. 1.

The isolated spectrum indicated by A(40) at the top of the graph corresponds to the fluorescence emission obtained 40 minutes after the addition of the bacteria to the solid organic matrix of the invention placed on the slide glass A, whereas the dense spectra at the lower part of the graph correspond to the other measurements made, as described hereinabove. Specifically, for the purpose of easy comparison, the double-maxima spectrum designated by the letter F relates to the fluorescence emission of the heated, red organic matrix placed on slide glass F.

It is apparent from FIG. 1 that the agar matrix comprising the polydiacetylene and the lipid has responded to the presence of the *e. coli*, as evident from the characteristic fluorescence spectrum measured 40 minutes after the addition of the bacteria to the matrix.

Example 19

Detecting the Presence of Bacteria in Urine Sample

Aliquots (40 µl) taken from stock solutions that were used for the growth of *E. coli* and *salmonella* strains were added into a 2 cc urine sample collected from a healthy man. The number of the bacteria in each aliquot was estimated to be approximately one million. The resulting spiked urine sample is placed on the surface of the organic matrix prepared according to Example 1. The Petri dish containing the organic matrix is transferred to an incubator at 27° C. After several hours, a clear blue to red color transition was observed. In contrast, the control Petri dish (containing the organic matrix which was contacted with a non-spiked urine sample) did not display a similar color change.

Example 20

Detecting the Presence of Bacteria in a Platelet Sample

Aliquots (40 µl) taken from stock solutions that were used for the growth of *E. coli* and *salmonella* strains were added into a 2 cc solutions extracted from a fresh (less than 2-day old) platelet donation (obtained from the blood bank). The number of the bacteria in each aliquot was estimated to be approximately one million. The resulting spiked platelet sample is mixed with an equal volume of a PBS buffer [pH=7] and placed on the surface of the organic matrix prepared according to Example 1. The Petri dish containing the organic matrix is transferred to an incubator at 27° C. After several hours, a clear blue to red color transition was observed. In contrast, the control Petri dish (containing the organic matrix which was contacted with a non-spiked platelet solution) did not display a similar color change.

Example 21

Use of Calorimetric Detectors for Distinguishing Between Different Bacterial Species Two calorimetric detectors were prepared according to the procedure of Example 1. In the first detector, the organic matrix contained the lipid dimyristoylphosphatydilcholine (DMPC) whereas in the second detector the lipid used was dimyristoylphosphatydilglycerole (DMPG). Four strains of bacteria were tested. The *Salmonella typhimurium* Phop-constitutive mutant was prepared as described previously (Qimron et al., *Cellular Microbiology* (2004), 6, 1057-1070). The wild type *Salmonella typhimurium* strain and the *E. coli* strains (*E. coli* B and *E. coli* K12) used were standard laboratory strains.

Figure 2:
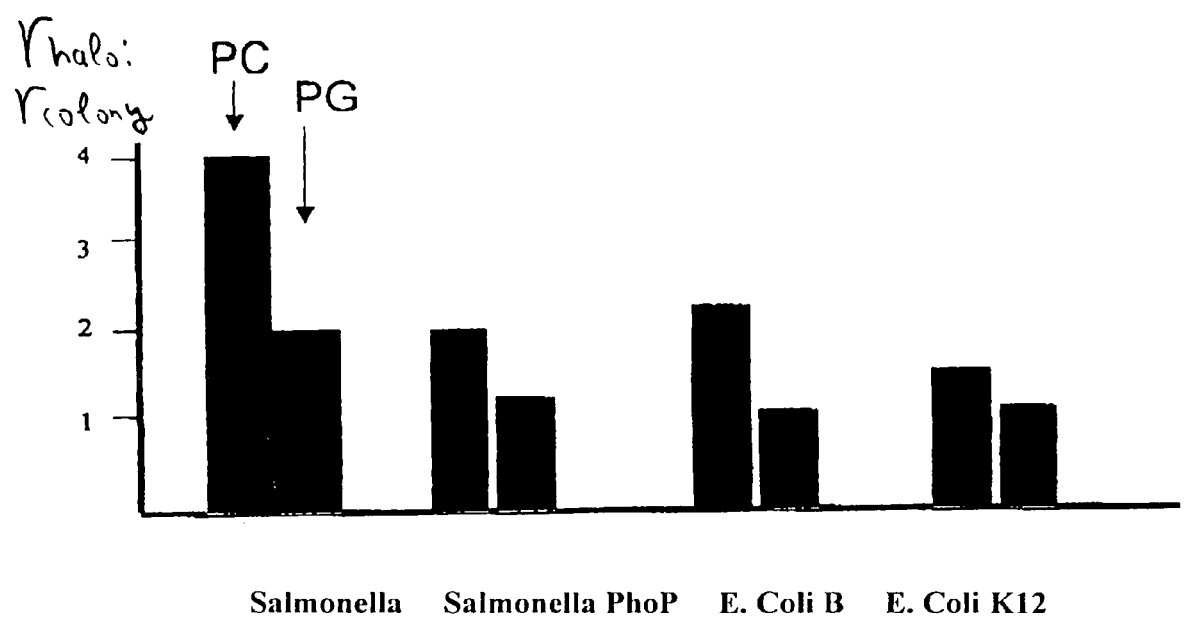
FIG. 2 depicts the calculated ratios between the diameters of various bacterial colonies inducing color changes in the organic matrices of the present invention and the diameters of the corresponding red halos surrounding said colonies.

Bacterial colonies were grown on conventional LB-agar overnight. Following growth, bacterial colonies were initiated on two Petri plates containing the detectors by touching the parent colonies with a sterilized wooden stick and gently touching of the surface of the detector. The plates were then placed at 22° C., and colonies as well as halos could be observed after 12-18 hours of incubation. The radius of each colony and the radius of the total area occupied by said colony together with its surrounding halo were measured by either direct measurement on the bacterial plate or by the use of image analysis methods. FIG. 2 is a bar diagram, wherein each pair of adjacent bars, from left to right, corresponds to the following set of calculated ratios:

$$\{r_{halo}{:}r_{colony}(1), r_{halo}{:}r_{colony}(2)\}_{salmonella}$$

$$\{r_{halo}{:}r_{colony}(1), r_{halo}{:}r_{colony}(2)\}_{salmonella\ PhoP}$$

$$\{r_{halo}{:}r_{colony}(1), r_{halo}{:}r_{colony}(2)\}_{E.\ Coli\ B}$$

$$\{r_{halo}{:}r_{colony}(1), r_{halo}{:}r_{colony}(2)\}_{E.\ Coli\ K12}$$

wherein the integers 1 and 2 designate the first and second organic matrices identified above (which contain either DMPC or DMPG, respectively).

Example 22

Preparation of Organic Matrix Containing Polydiacetylenes, Lipid and an Antibiotic Agent In this example, the following three bacterial strains were used:

1) *Salmonella serovar typhimurium* 1a (cs093)
2) *Salmonella serovar typhimurium* 1a-Mutant (Kanamycin resistant)
3) *Escherichia coli* MC4100 (streptomycin resistant)

Cell Growth:

*Salmonella* 1a was grown in liquid culture Luria-Bertani (LB- standard medium) over night at 37° c. *E. coli* MC4100 was grown over night at 37° c. in LB medium supplemented streptomycin (10 µg/ml). *Salmonella*-1a mutant was grown over night at 37° C. in LB medium supplemented Kanamycin (40 µg/ml).

Liposome Preparation:

The procedure was similar to the one described in Example 1. The molar ratio between the lipid (DMPC) and the tricosadionic acid monomer was 2:3. The concentration the samples prepared was 5 mM. The samples were dried in vacuo, to remove the organic solvents, and following the addition of 2 ml of deionized water, the resulting aqueous suspension was subjected to sonication at a temperature of 70° C. for 2 to 3 minutes by means of a probe-sonicator.

Blue LB-Agar Plate Preparation:

The hot vesicles containing DMPC and the monomer obtained as described above are added to hot LB-Agar (medium for bacteria growth), followed by addition of the antibiotic compounds [streptomycin (10 µg/ml) and kanamycin (40 µg/ml)]. The mixture was then cooled and kept at 4° c. several hours, followed by polymerization by irradiation at 254 nm for 0.7 minutes.

Experiment

All strains were grown on blue LB-Agar plate, on blue Lb-Agar plate supplemented streptomycin (10 µg/ml) and on blue Lb-Agar plate supplemented Kanamycin (40 µg/ml) at 25° c. for 12-19 hours. The blue to red color change was observed in those LB-agar plates wherein strains that were resistant to the antibiotic agent present in the agar were grown.

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. A colorimetric, fluorescent, or colorimetric and fluorescent detector for detecting the presence of bacteria, wherein the detector comprises:
   a gel-like solid organic matrix comprising one or more organic polymers that are capable of forming a gel-like solid organic matrix at room temperature, said polymers being selected from the group consisting of polysaccharides and polyacrylamides;
   one or more polydiacetylenes produced by polymerization of one or more diacetylene monomers;
   one or more lipids; and
   one or more nutrients required for the growth of the bacteria;
   wherein said diacetylene monomers and said lipids are in a molar ratio in the range of 1:10 to 3:2.

2. The detector according to claim 1, wherein the gel-like solid organic matrix is selected from the group consisting of agar, agarose and other natural or synthetic gelatinous polymers.

3. The detector according to claim 2, wherein the gel-like solid is agar, which contains nutrients required for the growth of the bacteria.

4. The detector according to claim 1, which further comprises one or more antibiotic compounds.

5. The detector according to claim 1, wherein the polydiacetylene(s) and the lipid(s) are homogeneously distributed within the organic matrix.

6. A radiation-polymerizable mixture comprising one or more diacetylene monomers, one or more lipids, one or more nutrients required for the growth of bacteria, and a gel-like solid organic matrix comprising one or more organic polymers that are capable of forming a gel-like solid organic matrix at room temperature,
wherein said diacetylene monomers and said lipids are in a molar ratio in the range of 1:10 to 3:2 and said organic polymers are selected from the group consisting of polysaccharides and polyacrylamides, and
wherein said mixture is suitable for use as a precursor for forming the detector according to claim 1.

7. The radiation-polymerizable mixture according to claim 6, wherein said one or more lipids are selected from the group consisting of phospholipids, lipopolysaccharides, steroids and/or mixtures thereof.

8. The radiation-polymerizable mixture according to claim 7, wherein said one or more lipids are selected from the group consisting of dimirystoylphosphatidylcholine (DMPC), phosphatidylglycerole (PG), dipalmitoylphosphatidylcholine (DPPC), natural phosphatidylcholine (PC), dimirystoylphosphatidylethanolamine (DMPE), cardiolipin, dimyristoylphosphatidylserine (DMPS), sphingomyelin, sphingolipids, ceramide, galactosylceramide, cholesterol, and mixtures thereof.

9. The radiation-polymerizable mixture according to claim 6, wherein said one or more lipids are selected from the group consisting of phospholipids, lipopolysaccharides, steroids and/or mixtures thereof.

10. The detector according to claim 1, wherein the nutrients required for the growth of bacteria are selected from the group consisting of yeast extract, broth, NaCl, and peptone.

11. The detector according to claim 1, which responds to the presence of bacteria by exhibiting a chromatic transition and/or fluorescence emission following an incubation period of said bacteria, wherein said incubation period is less than the period of time required for the development of visible bacterial colonies on said detector.

12. The detector according to claim 1, which responds to the presence of bacteria by exhibiting a chromatic transition and/or fluorescence emission following an incubation period of said bacteria, wherein the incubation time varies between 3 to 13 hours.

13. The detector according to claim 1, wherein the polydiacetylenes are obtained from diacetylene monomers selected from the group consisting of 10,12-tricosadiynoic acid, 10,12-pentacosadiynoic acid, 10,12-octadecadiynoic acid, 5,7-docosadiynoic acid, 5,7-pentacosadiynoic acid and 5,7-tetracosadiynoic acid; and the lipid is selected from the group consisting of dimirystoylphosphatidylcholine (DMPC), phosphatidylglycerole (PG), dipalmitoylphosphatidylcholine (DPPC), natural phosphatidylcholine (PC), dimirystoylphosphatidylethanolamine (DMPE), cardiolipin, dimyristoylphosphatidylserine (DMPS), sphingomyelin, sphingolipids, ceramide, galactosylceramide, cholesterol, and mixtures thereof.

14. The detector according to claim 1 wherein said one or more lipids are selected from the group consisting of phospholipids, lipopolysaccharides, steroids and/or mixtures thereof.

15. The detector according to claim 14, wherein said one or more lipids are selected from the group consisting of dimirystoylphosphatidylcholine (DMPC), phosphatidylglycerole (PG), dipalmitoylphosphatidylcholine (DPPC), natural phosphatidylcholine (PC), dimirystoylphosphatidylethanolamine (DMPE), cardiolipin, dimyristoylphosphatidylserine (DMPS), sphingomyelin, sphingolipids, ceramide, galactosylceramide, cholesterol, and mixtures thereof.

16. The colorimetric, fluorescent, or colorimetric and fluorescent detector according to claim 1, wherein said one or more lipids are selected from the group consisting of phospholipids, lipopolysaccharides, steroids and/or mixtures thereof.

17. A colorimetric, fluorescent, or colorimetric and fluorescent detector, comprising a solid organic matrix at room temperature that includes one or more polydiacetylene(s), one or more lipid(s), and one or more nutrients required for the growth of bacteria, wherein said detector is prepared by:
providing a suspension containing one or more diacetylene monomers and one or more lipids, said diacetylene monomers and said lipids being in a molar ratio in the range of 1:10 to 3:2,
mixing said suspension with a liquid precursor of the solid organic matrix, said liquid precursor comprising one or more polymers selected from the group consisting of polysaccharides and polyacrylamides, and further comprising one or more nutrients required for the growth of bacteria,
solidifying the resulting mixture, and
polymerizing the diacetylene monomer(s) present therein, to obtain a solid organic matrix comprising chromatic polydiacetylene(s), lipids(s), and nutrient(s) required for the growth of bacteria.

18. The colorimetric, fluorescent, or colorimetric and fluorescent detector according to claim 17, wherein said one or more lipids are selected from the group consisting of phospholipids, lipopolysaccharides, steroids and/or mixtures thereof.

19. The colorimetric, fluorescent, or colorimetric and fluorescent detector according to claim 18, wherein said one or more lipids are selected from the group consisting of dimirystoylphosphatidylcholine (DMPC), phosphatidylglycerole (PG), dipalmitoylphosphatidylcholine (DPPC), natural phosphatidylcholine (PC), dimirystoylphosphatidylethanolamine (DMPE), cardiolipin, dimyristoylphosphatidylserine (DMPS), sphingomyelin, sphingolipids, ceramide, galactosylceramide, cholesterol, and mixtures thereof.

20. The colorimetric, fluorescent, or colorimetric and fluorescent detector according to claim 17, wherein said one or more lipids are selected from the group consisting of phospholipids, lipopolysaccharides, steroids and/or mixtures thereof.

* * * * *